(12) United States Patent
Eblacas et al.

(10) Patent No.: US 8,945,200 B1
(45) Date of Patent: Feb. 3, 2015

(54) ILIAC BIFURCATED ENDOPROSTHESIS MEDICAL APPARATUS AND METHOD OF DEPLOYING SAME

(71) Applicant: W.L. Gore & Associates, Inc., Newark, DE (US)

(72) Inventors: Julio E. Eblacas, Milpitas, CA (US); Linda N. Elkins, Redwood City, CA (US); William P. Witort, Berkeley, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 257 days.

(21) Appl. No.: 13/679,753

(22) Filed: Nov. 16, 2012

Related U.S. Application Data

(60) Provisional application No. 61/560,395, filed on Nov. 16, 2011.

(51) Int. Cl.
*A61F 2/06* (2013.01)
*A61F 2/954* (2013.01)

(52) U.S. Cl.
CPC .................................... *A61F 2/954* (2013.01)
USPC ....................................................... 623/1.12

(58) Field of Classification Search
USPC .................. 606/108; 623/1.11, 1.12, 1.23
See application file for complete search history.

(56) References Cited

U.S. PATENT DOCUMENTS

| | | | | |
|---|---|---|---|---|
| 5,591,228 A | * | 1/1997 | Edoga | 128/898 |
| 5,824,055 A | * | 10/1998 | Spiridigliozzi et al. | 623/1.11 |
| 6,183,504 B1 | * | 2/2001 | Inoue | 623/1.11 |
| 6,261,316 B1 | * | 7/2001 | Shaolian et al. | 623/1.11 |
| 6,352,561 B1 | | 3/2002 | Leopold et al. | |
| 6,440,161 B1 | * | 8/2002 | Madrid et al. | 623/1.11 |
| 6,478,813 B1 | * | 11/2002 | Keith et al. | 623/1.11 |
| 6,520,986 B2 | | 2/2003 | Martin et al. | |
| 6,641,606 B2 | * | 11/2003 | Ouriel et al. | 623/1.12 |
| 6,676,694 B1 | * | 1/2004 | Weiss | 623/1.11 |
| 6,689,157 B2 | * | 2/2004 | Madrid et al. | 623/1.11 |
| 6,849,087 B1 | * | 2/2005 | Chuter | 623/1.23 |
| 7,419,501 B2 | | 9/2008 | Chiu et al. | |
| 7,682,380 B2 | | 3/2010 | Thornton et al. | |
| 7,753,945 B2 | | 7/2010 | Bruun et al. | |
| 7,998,186 B2 | * | 8/2011 | Hartley | 623/1.11 |
| 8,012,193 B2 | * | 9/2011 | Hartley et al. | 623/1.11 |
| 8,092,468 B2 | | 1/2012 | Hansen | |
| 8,357,192 B2 | * | 1/2013 | Mayberry et al. | 623/1.11 |

(Continued)

FOREIGN PATENT DOCUMENTS

WO 2012/024308 2/2012

OTHER PUBLICATIONS

Kasirajan K, Gupta N. Technical Tips for Successful Outcomes Using Adjunctive Procedures During Endovascular Aortic Aneurysm Repair. Semin Vasc Surg 2012; 25:161-166.

(Continued)

*Primary Examiner* — Ryan Severson
*Assistant Examiner* — Jonathan W Miles
(74) *Attorney, Agent, or Firm* — Gilbert R. Gabo

(57) ABSTRACT

Devices and methods for the endovascular repair of aneurysms approximate to side branch vessels and more particularly to devices and methods for placing an acutely angled bifurcated stent graft.

11 Claims, 9 Drawing Sheets

(56) References Cited

U.S. PATENT DOCUMENTS

| | | | |
|---|---|---|---|
| 2003/0120330 A1* | 6/2003 | Ouriel et al. | 623/1.12 |
| 2004/0138734 A1 | 7/2004 | Chobotov et al. | |
| 2004/0143316 A1* | 7/2004 | Spiridigliozzi et al. | 623/1.13 |
| 2005/0033402 A1 | 2/2005 | Cully et al. | |
| 2005/0033416 A1* | 2/2005 | Seguin et al. | 623/1.23 |
| 2007/0219614 A1* | 9/2007 | Hartley | 623/1.11 |
| 2007/0299495 A1 | 12/2007 | Zukowski et al. | |
| 2008/0269866 A1 | 10/2008 | Hamer et al. | |
| 2010/0211052 A1 | 8/2010 | Brown et al. | |
| 2011/0270375 A1* | 11/2011 | Hartley et al. | 623/1.11 |
| 2011/0270376 A1* | 11/2011 | Hartley | 623/1.11 |

OTHER PUBLICATIONS

Kotsis T, Tsanis A, Sfyroeras G, Lioupis C, Moulakakis K, Georgakis P. Endovascular Exclusion of Symptomatic Bilateral Common Iliac Artery Aneurysms With Preservation of an Aneurysmal Internal Iliac Artery via a Reverse-U Stent-Graft. J Endovasc Ther, 2006; 13:158-163.

Minion DJ, Xenos E, Sorial E, Saha S, Endean E. The Trifurcated Endograft Technique for Hypogastric Preservation During Endovascular Aneurysm Repair. J Vasc Surg 2008; 47:658-61.

Serracino-Inglott F, Bray AE, Myers P. Endovascular Abdominal Aortic Aneurysm Repair in Patients with Common Iliac Artery Aneurysm—Initial Experience with the Zenith Bifurcated Iliac Side Branch Device. J Vasc Surg 2007; 46:211-217.

\* cited by examiner

ILIAC BIFURCATED ENDOPROSTHESIS MEDICAL APPARATUS AND METHOD OF DEPLOYING SAME

CROSS-REFERENCE TO RELATED APPLICATIONS

This application claims priority to U.S. Provisional Application Ser. No. 61/560,395, which was filed on Nov. 16, 2011 and is hereby incorporated by reference in its entirety.

BACKGROUND

1. Field

The present disclosure generally relates to a delivery system and method for delivering an expandable endoluminal prosthetic device such as a stent graft and more particularly to a device and method for placing an acutely angled bifurcated stent graft.

2. Discussion of the Related Art

Expandable surgical devices such as stents or stent grafts are used in a variety of places in the human body to repair aneurysms and to support various anatomical lumens, such as blood vessels, respiratory ducts, gastrointestinal ducts, and the like.

Conventionally, these devices are deployed across an aneurysm or in the regions of a stenosis in the target body lumen to repair the aneurysm or to hold the lumen open. Because stent graft implantation is a relatively non-invasive procedure, it has been proven to be a favorable alternative to surgery in, for example, the repair of an aneurysm. Bifurcated devices with their trunk and branching configuration are particularly well suited for use in branching body lumen systems, such as in the coronary vasculature, and the peripheral vasculature. The coronary vasculature includes the right, left common, left anterior descending and circumflex arteries and their branches. The peripheral vasculature includes branches of the carotids, aorta, femoral, popliteal, internal iliac, or hypogastric and related arteries. Placement of such a bifurcated device often involves approaching the bifurcated section of the artery through at least two vessels.

There exists a need for a stent graft delivery system which would allow placement of multiple bifurcated and single lumen stent grafts into an acutely angled or "reverse direction" branches, as for example a repair of the hypogastric artery. A simplified surgical procedure, suitable for complex target sites, would decrease the number or size of incisions, reduce the required surgical steps, and thereby reduce patient trauma associated with a more complex medical procedure.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

DETAILED DESCRIPTION

Proximal as used herein indicates a position closest to a practitioner and distal indicates a position furthest from a practitioner.

In accordance with various embodiments, a method of endoluminally deploying a branched stent assembly to branched vasculature is generally illustrated in FIGS. 1-9. Methods of fabricating various branched and non-branched stent assemblies, as well as delivery devices and methods are disclosed in U.S. Pat. No. 6,520,986, U.S. Pat. No. 7,682,380, U.S. Pat. No. 6,352,561 and U.S. Publication 2008/0269866, hereby incorporated by reference in their entirety.

Figure 1:
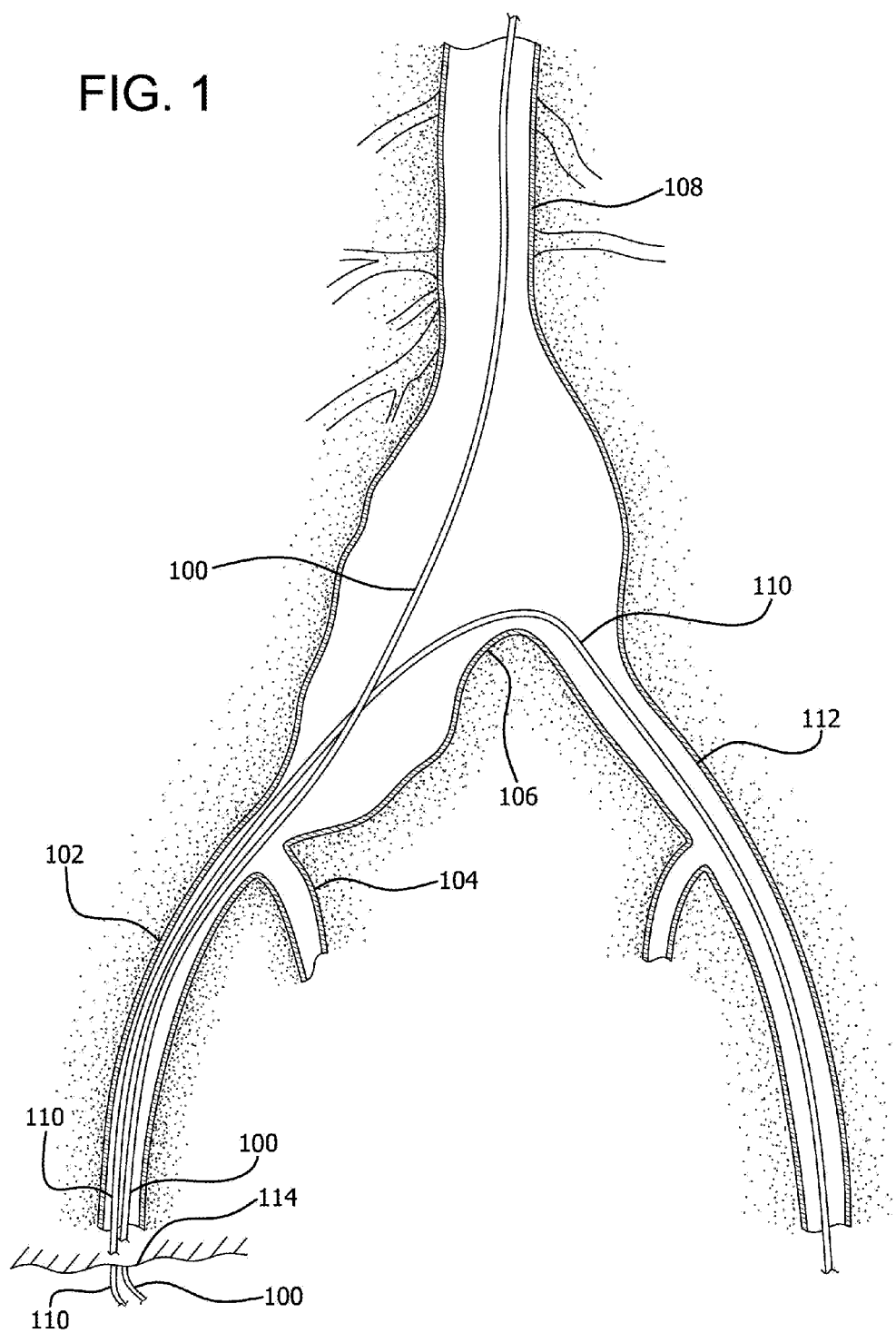
FIGS. 1-9 illustrate various embodiments of methods of deploying a branched stent assembly to branched vasculature.

As shown in FIG. 1, the method includes positioning a first guidewire 100 through a first femoral artery 102 having a hypogastric side branch 104. The first guidewire 100 passes an aortic bifurcation 106 and extends into a descending aorta 108. A second guidewire 110 is positioned through the first femoral artery 102, across the aortic bifurcation 106 and through a second femoral artery 112. A first compacted, expandable, bifurcated device having a main body through lumen, a side branch lumen, an extended first branch and a contralateral leg is prepared for implantation external to the patient. The compacted device (not shown in FIG. 1) is placed onto the first 100 and second 110 guidewire external to the access site 114. The first guidewire 100 is routed into the compacted device main body through lumen. The second guidewire 110 is routed into the compacted device side branch lumen.

Figure 2:
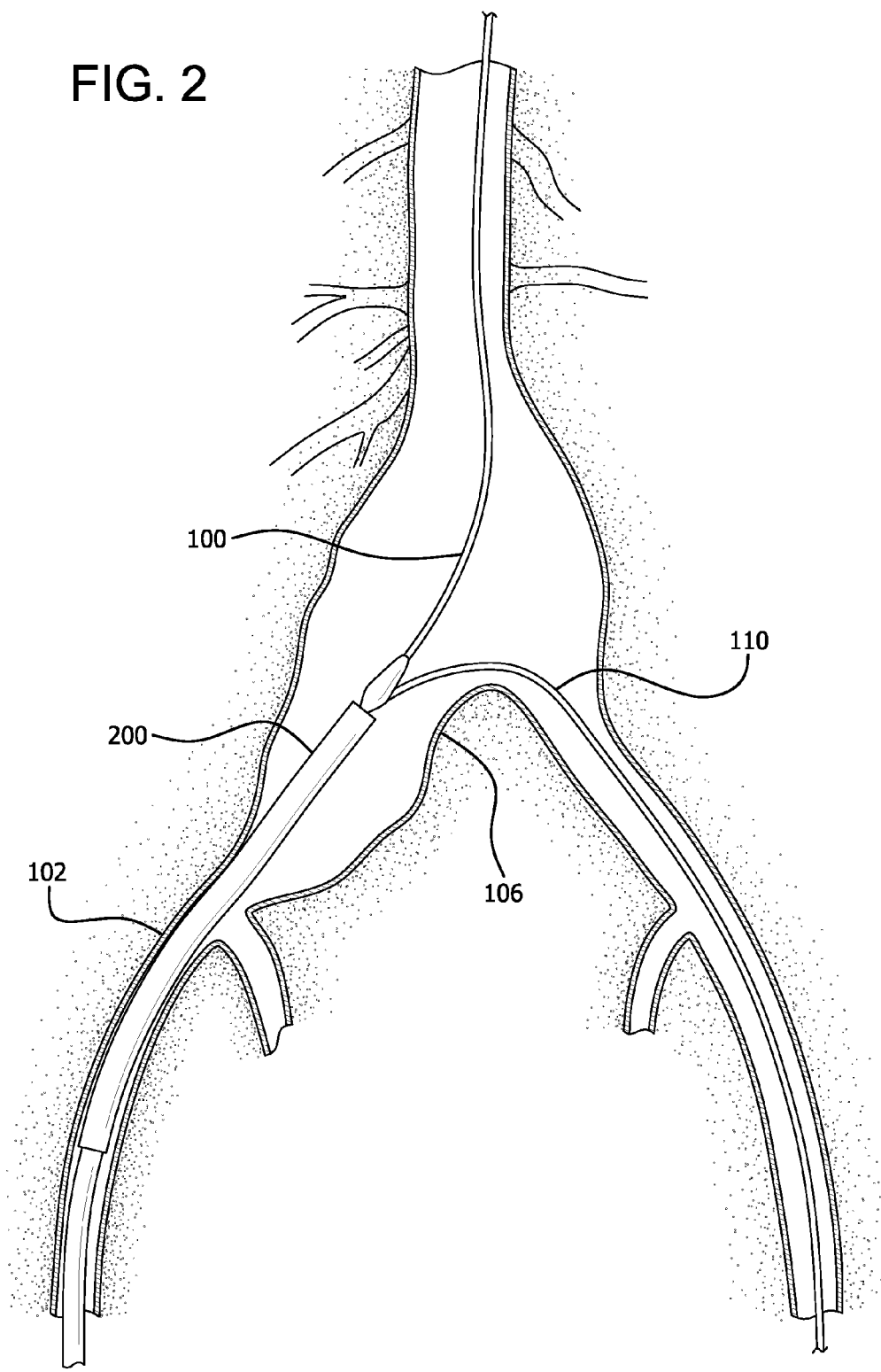

As shown in FIG. 2, the first compacted device 200 is advanced along the first and second guidewires 100, 110 within the first femoral artery 102 to a position adjacent to the aortic bifurcation 106.

Figure 3:
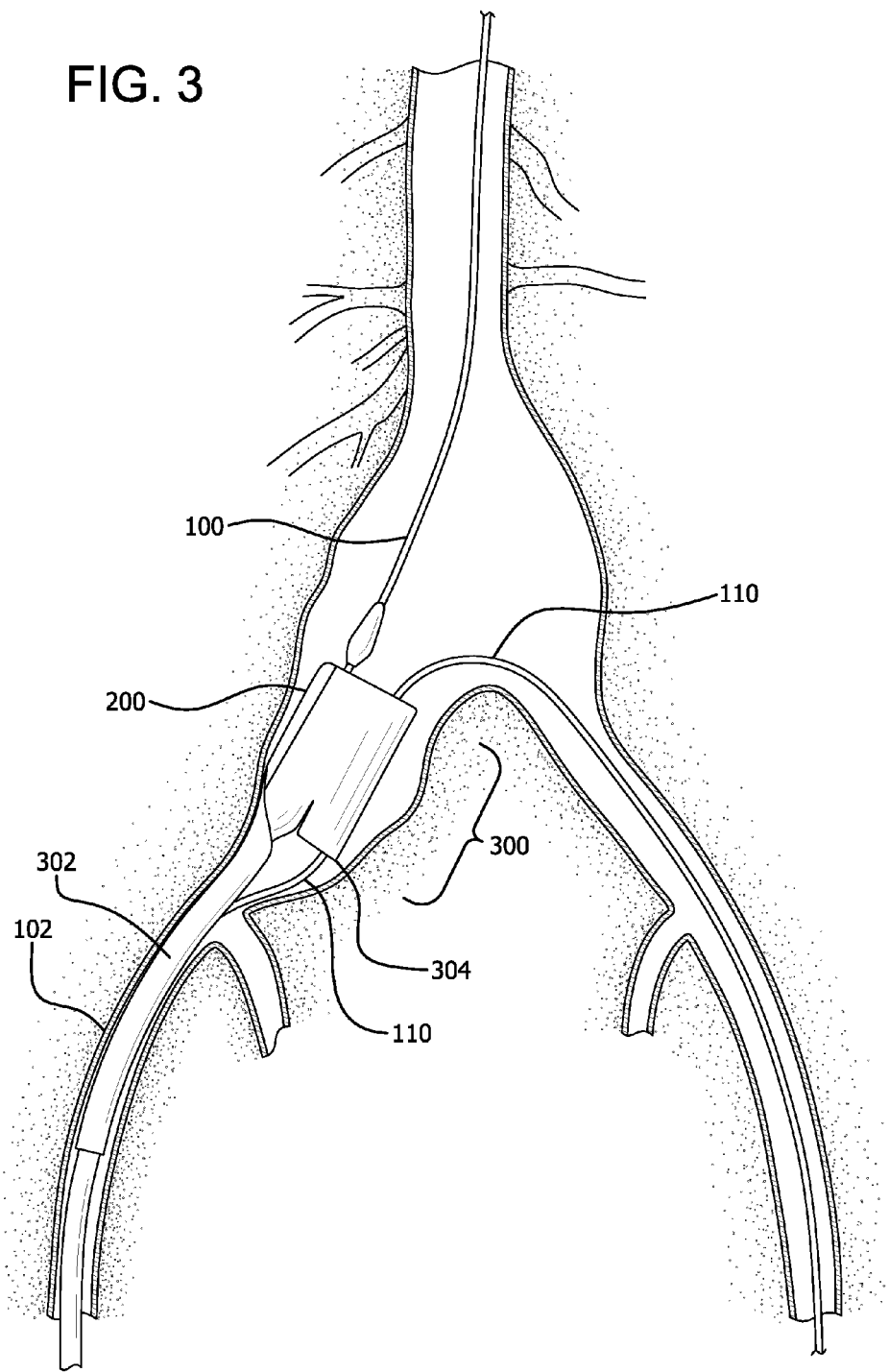

As shown in FIG. 3, the distal end 300 of the first compacted expandable device 200 is deployed, so that the compacted extended first branch 302 of the first compacted expandable device 200 is located within the first femoral artery 102 and the contralateral leg 304 of the first compacted expandable device 200 is exposed.

Figure 4:
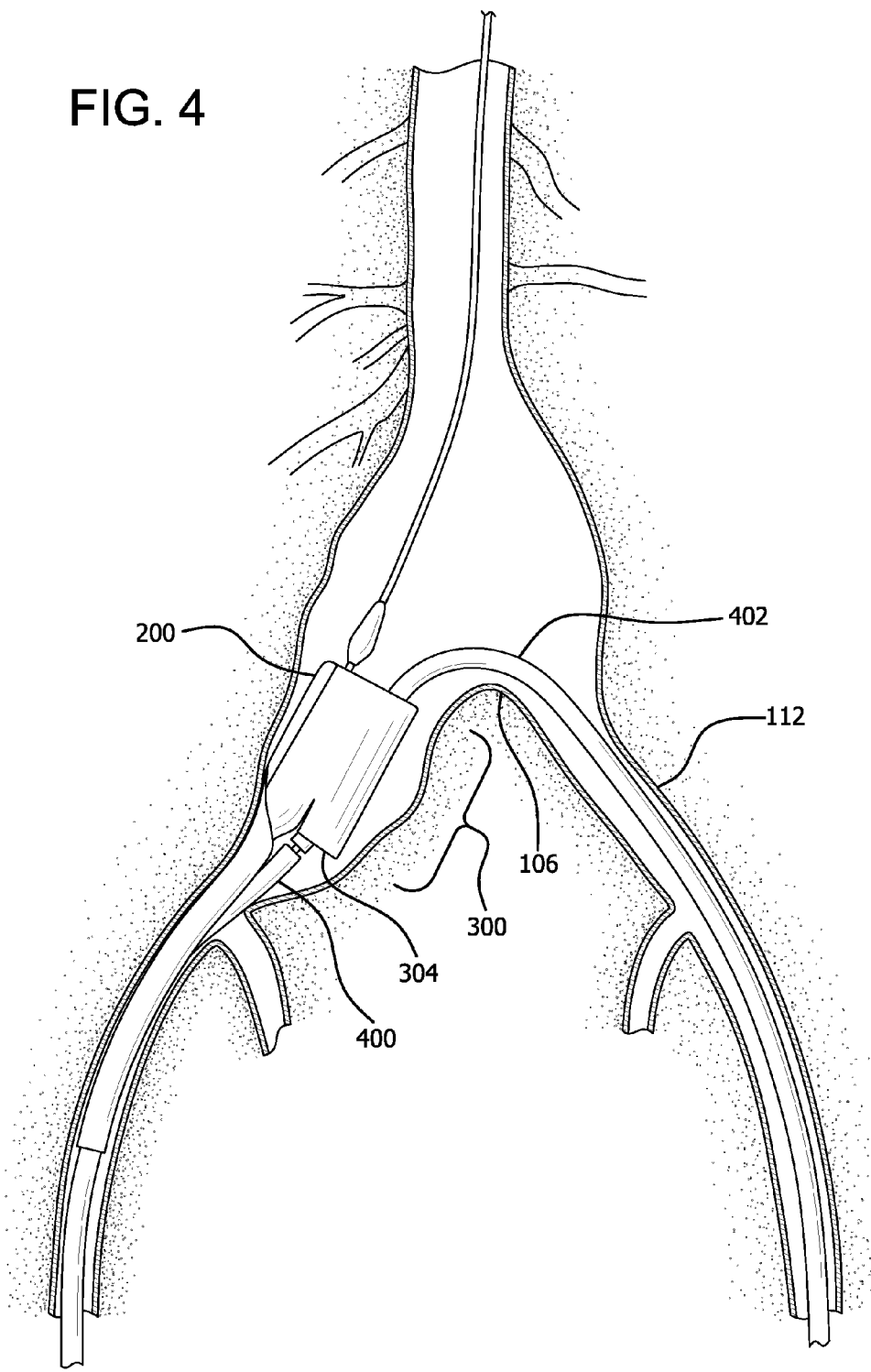

As shown in FIG. 4, a dilator 400 and delivery sheath 402 is advanced along the second guidewire, through the second femoral artery 112, across the aortic bifurcation 106, through the distal end 300 of the first expandable device 200 and through the exposed contralateral leg 304.

Figure 5:
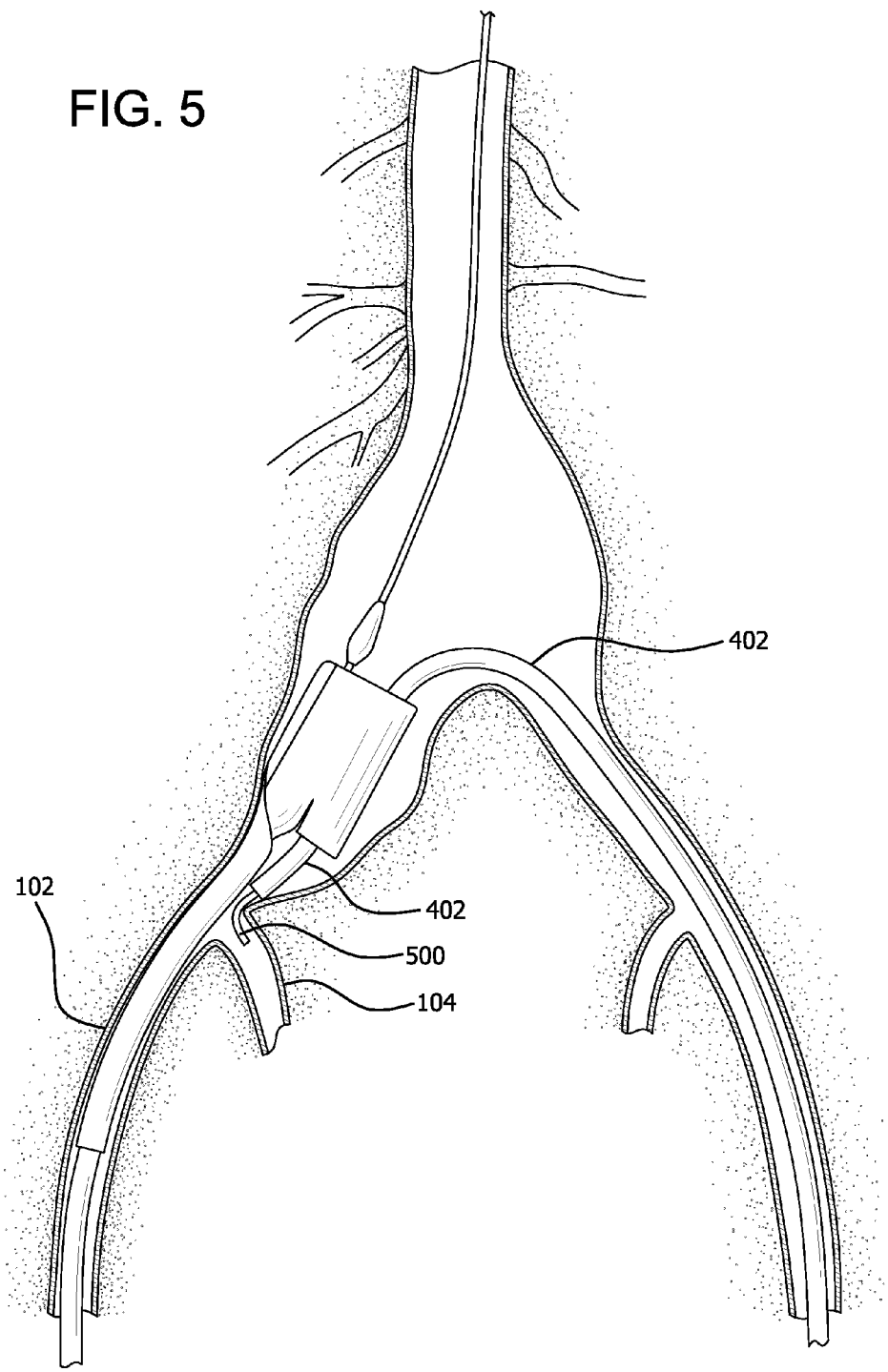

As shown in FIG. 5, the dilator 400 (from FIG. 4) and the second guidewire are withdrawn from the delivery sheath 402. The delivery sheath 402 is further advanced to a position approximate the hypogastric side branch 104. A third guidewire 500 is advanced through the delivery sheath 402 and into the hypogastric side branch 104 of the first femoral artery 102.

Figure 6:
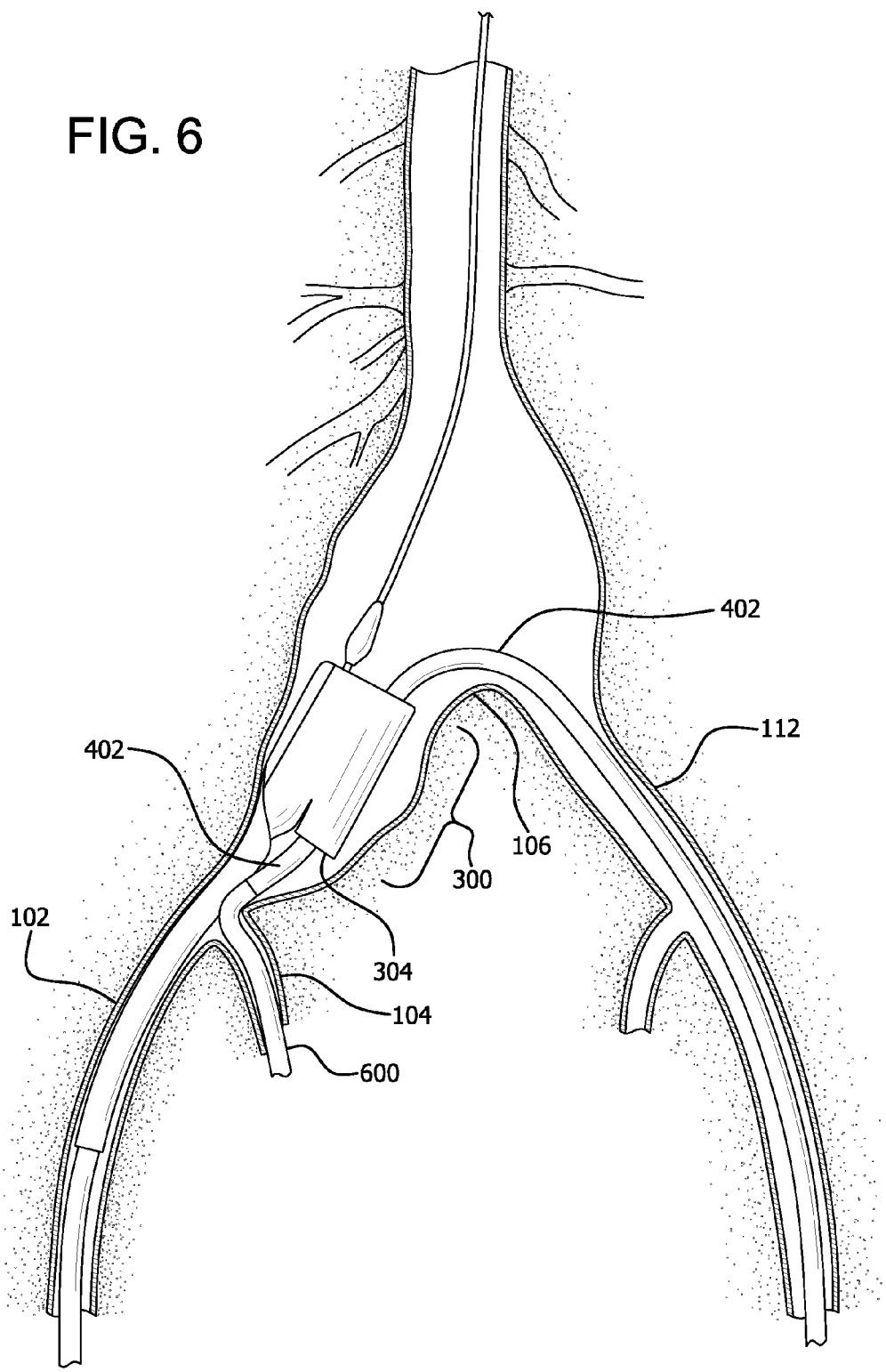

As shown in FIG. 6, a second compacted, expandable device 600, having a single main body through lumen is advanced through the delivery sheath 402 along the third guidewire, through the second femoral artery 112, across the aortic bifurcation 106, through the distal end of the expandable device 300, through the exposed contralateral leg 304 and into the hypogastric side branch 104 of the first femoral artery 102.

Figure 7:
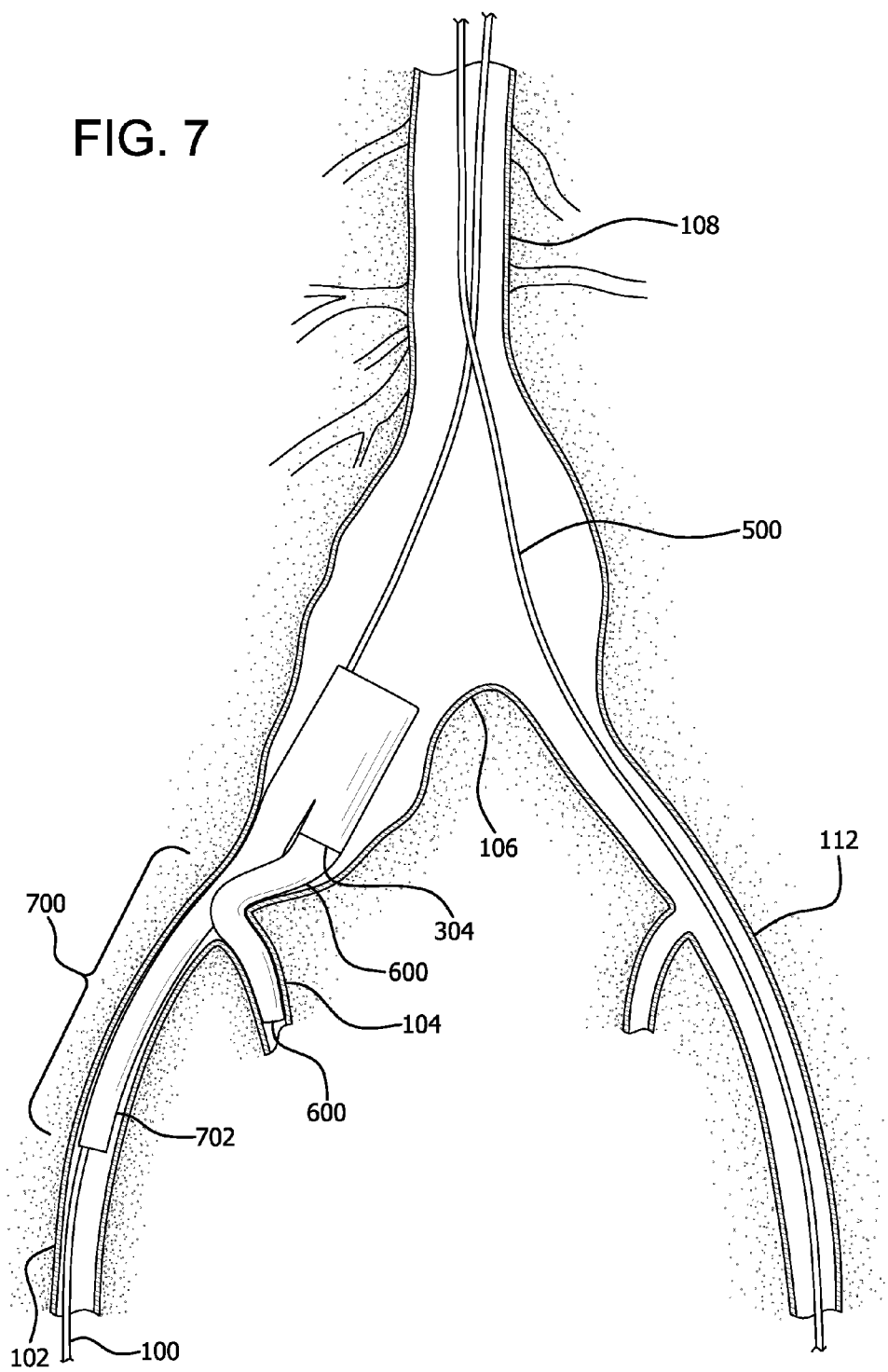

As shown in FIG. 7, the second compacted device 600 is deployed so that the second device 600 expands into the exposed contralateral leg 304 and into the hypogastric side branch 104 of the first femoral artery 102. The proximal end 700 of the first compacted, expandable, bifurcated device 200 is deployed so that the extended first branch 702 is positioned into the first femoral artery 102 and crosses the hypogastric side branch 104 of the first femoral artery 102. The delivery sheath 402 (from FIG. 6) is fully withdrawn along the second femoral artery 112. The third guidewire 500 is partially retracted along the second femoral artery 112 and then advanced past the aortic bifurcation 106 and into the descending aorta 108.

Figure 8:
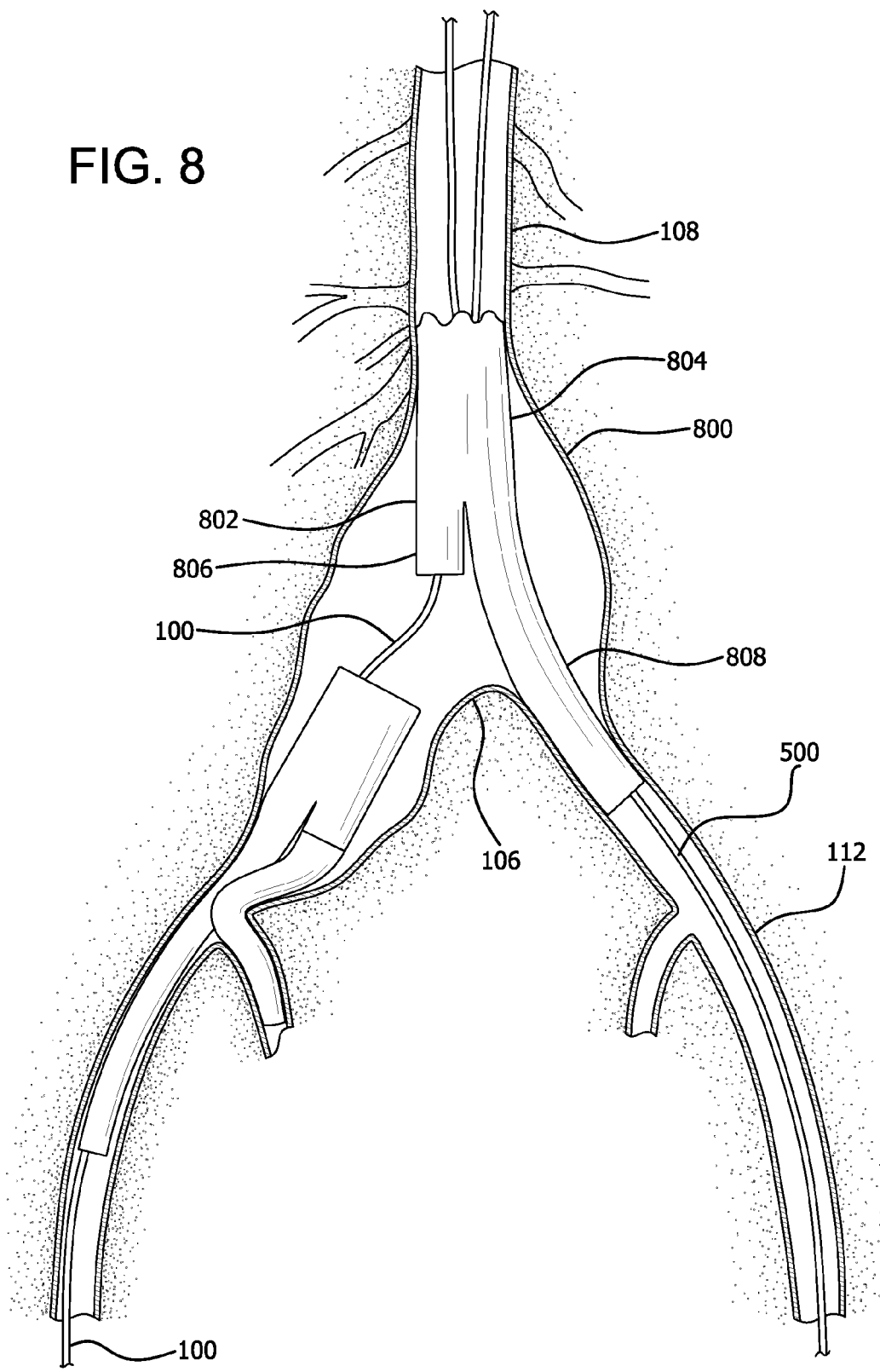

As depicted in FIG. 8, the first guidewire 100 is partially retracted to a position approximate to the aortic bifurcation 106. A third compacted, expandable, bifurcated device having a main body through lumen, a side branch lumen, an extended first branch and a contralateral leg is advanced over the third guidewire 500, within the second femoral artery 112, into the descending aorta 108 to a position distal to the aneurysm 800. The third device 802 is deployed so that the main body 804 is expanded into the descending aorta 108 distal to the aneurysm 800 The contralateral leg 806 of the third device 802 is exposed and the extended first branch 808 of the third device 802 is expanded into the second femoral artery 112. The first guidewire 100 is advanced past the aortic bifurcation 106 and into the exposed contralateral leg 806 of the third device 802.

Figure 9:
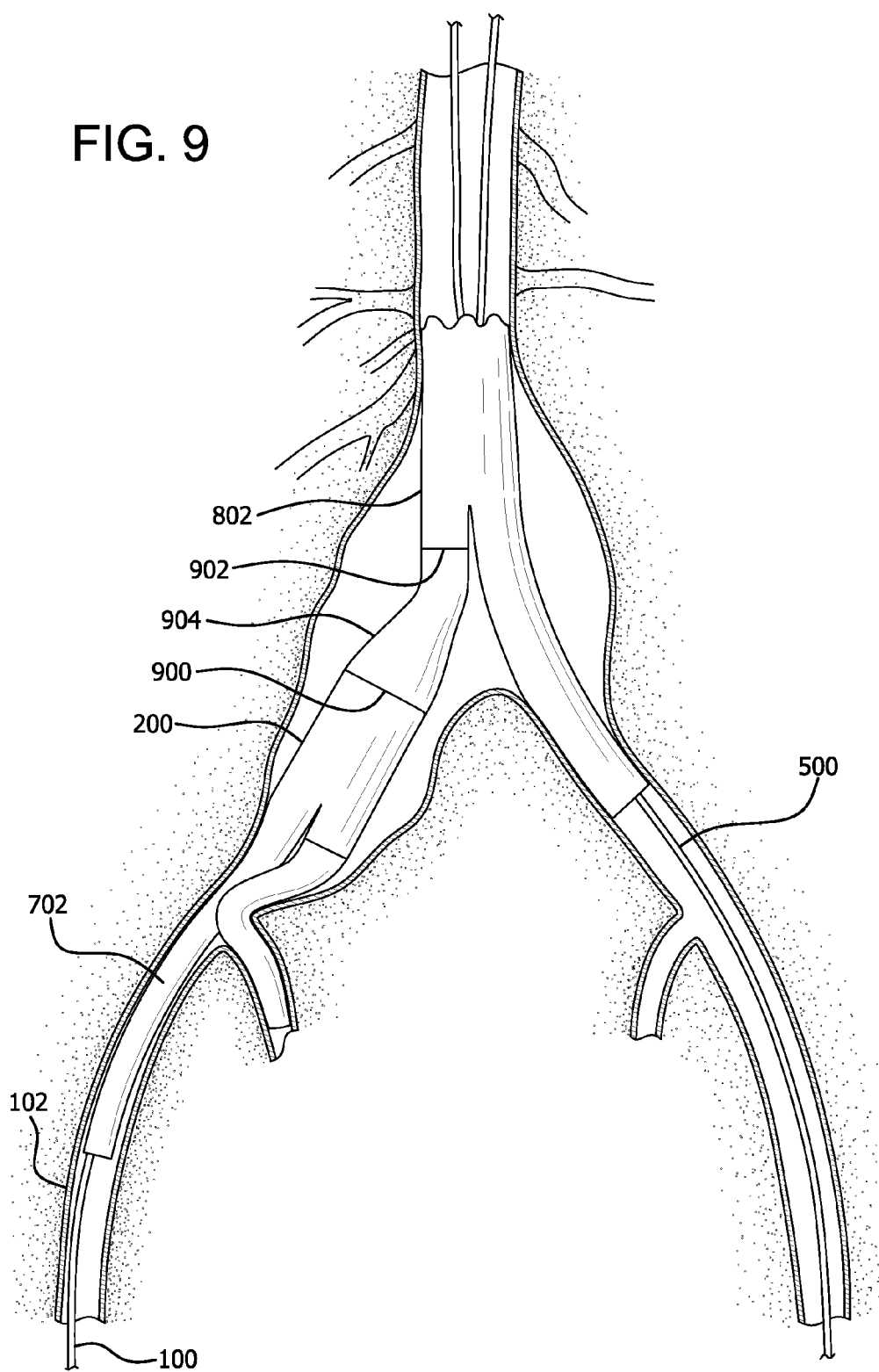

As shown in FIG. 9, a fourth compacted, expandable device having a single main body through lumen is advanced over the first guidewire 100 within the first femoral artery 102, through the extended first branch 702 of the first expandable device 200, through the distal end 900 of the first expandable device 200 and into the exposed contralateral leg 902 of the third device 802. The fourth compacted device is deployed so that the fourth device 904 expands into the distal end 900 of the first device 200 and expands into the exposed contralateral leg 902 of the third device 802. To complete the procedure, the first and third guidewires 100, 500 are fully withdrawn.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A method for repairing an aneurysm, comprising:
   advancing a first guidewire through a first femoral artery, part an internal iliac artery adjacent the first femoral artery, and into a descending aorta;
   advancing a second guidewire through one of the first femoral artery, across an aortic bifurcation and toward the second femoral artery;
   inserting the first and second guidewires through a main body through lumen and a side branch lumen, respectively, of a bifurcated first device external to the patient;
   advancing the bifurcated first device along the first and second guidewires towards a common iliac bifurcation proximal to the first femoral artery;
   expanding at least a portion of the bifurcated first device to allow access through the side branch lumen;
   advancing a side branch delivery sheath along the second guidewire toward the common iliac bifurcation;
   advancing a third guidewire through the side branch delivery sheath and into the internal iliac artery;
   advancing a compacted, expandable second device having a single main body through lumen along the third guidewire into the internal iliac artery;
   deploying the second device in both the side branch lumen of the first device and the internal iliac artery;
   expanding a remaining portion of the bifurcated first device;
   withdrawing the side branch delivery sheath from the patient; and
   partially retracting the third guidewire along the second femoral artery and then advancing the third guidewire past the aortic bifurcation and into the aorta.

2. The method of claim 1 including retracting the first guidewire along the first femoral artery to a position approximate to the aortic bifurcation.

3. The method of claim 2 including providing a compacted, expandable, bifurcated third device having a main body through lumen, a side branch lumen, an extended first branch and a contralateral leg.

4. The method of claim 3 including advancing the third compacted, expandable, bifurcated device along the third guidewire, within the second femoral artery, into the aorta to a position distal to the aneurysm.

5. The method of claim 4 including deploying the third device so that the main body is expanded into the aorta distal to the aneurysm, the contralateral leg of the third device is exposed and the extended first branch of the third device is expanded into the second femoral artery.

6. The method of claim 5 including advancing the first guidewire past the aortic bifurcation and into the exposed contralateral leg of the third device.

7. The method of claim 6 including providing a compacted, expandable fourth device having a single main body through lumen.

8. The method of claim 7 including advancing the compacted, expandable fourth device along the first guidewire within the first femoral artery, through the extended first branch of the first device, through the distal end of the first device and into the exposed contralateral leg of the third device.

9. The method of claim 8 including deploying the fourth device so that the fourth device expands into the distal end of the first device and expands into the exposed contralateral leg of the third device.

10. The method of claim 9 including withdrawing the first and third guidewires.

11. A method of repairing an aneurysm, comprising:
    positioning a first guidewire through a first femoral artery having a hypogastric side branch, the guidewire passing an aortic bifurcation and into a descending aorta;
    positioning a second guidewire through the first femoral artery, across the aortic bifurcation and through a second femoral artery;
    providing a compacted, expandable, bifurcated first device having a main body through lumen, a side branch lumen, an extended first branch and a contralateral leg;
    inserting the first guidewire into the first device main body through lumen;
    inserting the second guidewire into the first device side branch lumen;
    advancing the first device along the first and second guidewires within the first femoral artery to a position adjacent to the aortic bifurcation;
    deploying a distal end of the first device, so that the compacted extended first branch is located within the first femoral artery and the contralateral leg is exposed;
    advancing a dilator and delivery sheath along the second guidewire, through the second femoral artery, across the aortic bifurcation, through the distal end of the first device and through the exposed contralateral leg;
    withdrawing the dilator and second guidewire from the delivery sheath;
    positioning a third guidewire through the delivery sheath and into the hypogastric side branch of the first femoral artery;
    providing a compacted, expandable second device having a single main body through lumen;
    advancing the second device through the delivery sheath along the third guidewire, through the second femoral artery, across the aortic bifurcation, through the distal end of the first device, through the exposed contralateral leg and into the hypogastric side branch of the first femoral artery;

deploying the second device so that the second device expands into the exposed contralateral leg and into the hypogastric side branch of the first femoral artery;

deploying the proximal end of the first device so that the extended first branch is positioned into the first femoral artery and crosses the hypogastric side branch of the first femoral artery;

withdrawing the delivery sheath along the second femoral artery;

partially retracting the third guidewire along the second femoral artery and then advancing the third guidewire past the aortic bifurcation and into the aorta;

retracting the first guidewire along the first femoral artery to a position approximate to the aortic bifurcation;

providing a compacted, expandable, bifurcated third device having a main body through lumen, a side branch lumen, an extended first branch and a contralateral leg;

advancing the third device along the third guidewire, within the second femoral artery, into the aorta to a position distal to the aneurysm;

deploying the third device so that the main body is expanded into the aorta distal to the aneurysm, the contralateral leg of the third device is exposed and the extended first branch of the third device is expanded into the second femoral artery;

advancing the first guidewire past the aortic bifurcation and into the exposed contralateral leg of the third device;

providing a compacted, expandable fourth device having a single main body through lumen;

advancing the fourth device along the first guidewire within the first femoral artery, through the extended first branch of the first device, through the distal end of the first device and into the exposed contralateral leg of the third device;

deploying the fourth device so that the fourth device expands into the distal end of the first device and expands into the exposed contralateral leg of the third device; and withdrawing the first and third guidewires.

* * * * *